US008067550B2

(12) United States Patent
Barden et al.

(10) Patent No.: US 8,067,550 B2
(45) Date of Patent: Nov. 29, 2011

(54) HYBRIDOMAS PRODUCING ANTIBODIES AGAINST NON FUNCTIONAL P2X7 RECEPTOR

(75) Inventors: Julian Alexander Barden, New South Wales (AU); Angus Gidley-Baird, New South Wales (AU)

(73) Assignee: Biosceptre International Limited, North Ryde, New South Wales (AU)

( * ) Notice: Subject to any disclaimer, the term of this patent is extended or adjusted under 35 U.S.C. 154(b) by 47 days.

(21) Appl. No.: 12/445,273

(22) PCT Filed: Oct. 10, 2007

(86) PCT No.: PCT/AU2007/001540
§ 371 (c)(1),
(2), (4) Date: Apr. 10, 2009

(87) PCT Pub. No.: WO2008/043145
PCT Pub. Date: Apr. 17, 2008

(65) Prior Publication Data
US 2010/0105068 A1    Apr. 29, 2010

(30) Foreign Application Priority Data

Oct. 10, 2006  (AU) .............................. 2006905591

(51) Int. Cl.
*C07K 16/00* (2006.01)
*C07K 16/28* (2006.01)
*C07K 16/30* (2006.01)
*C12P 21/08* (2006.01)
*A61K 39/395* (2006.01)
*A61K 39/00* (2006.01)

(52) U.S. Cl. ............. 530/388.1; 530/387.1; 530/388.22; 530/388.8; 424/130.1; 424/138.1; 424/141.1; 424/143.1; 435/326; 435/330

(58) Field of Classification Search .................. None
See application file for complete search history.

(56) References Cited

U.S. PATENT DOCUMENTS

| | | | |
|---|---|---|---|
| 6,133,434 A | 10/2000 | Buell et al. | |
| 6,303,338 B1 | 10/2001 | Ni et al. | |
| 6,306,393 B1 | 10/2001 | Goldenberg | |
| 6,329,503 B1 | 12/2001 | Afar et al. | |
| 6,709,832 B1 | 3/2004 | Von Knebel Doeberitz | |
| 7,183,064 B1 | 2/2007 | Slater et al. | |
| 7,326,415 B2 | 2/2008 | Barden et al. | |
| 7,531,171 B2 | 5/2009 | Barden et al. | |
| 7,767,789 B2 | 8/2010 | Gorodeski et al. | |
| 7,888,473 B2 | 2/2011 | Barden et al. | |
| 2007/0020706 A1 | 1/2007 | Gorodeski et al. | |
| 2007/0248963 A1 | 10/2007 | Slater et al. | |
| 2008/0131438 A1 | 6/2008 | Barden et al. | |
| 2008/0227122 A1 | 9/2008 | Barden et al. | |
| 2011/0092674 A1 | 4/2011 | Barden et al. | |

FOREIGN PATENT DOCUMENTS

| | | |
|---|---|---|
| AU | 64184/98 B2 | 10/1998 |
| CA | 2284859 C | 1/2007 |
| EP | 1006186 A1 | 10/1998 |
| WO | WO 92/16558 A1 | 10/1992 |
| WO | WO 95/33048 A2 | 12/1995 |
| WO | WO 97/06256 A2 | 2/1997 |
| WO | WO 97/41222 A1 | 11/1997 |
| WO | WO 98/42835 A1 | 10/1998 |
| WO | WO 00/050458 A1 | 8/2000 |
| WO | WO 01/06259 A1 | 1/2001 |
| WO | WO 01/30964 A2 | 5/2001 |
| WO | WO 02/57306 | 7/2002 |
| WO | WO 02/057306 A1 | 7/2002 |
| WO | WO 03/002762 | 3/2003 |
| WO | WO 2004/092384 | 10/2004 |
| WO | WO 08/043145 A2 | 4/2008 |
| WO | WO 08/043146 A1 | 4/2008 |

OTHER PUBLICATIONS

Barden J. A. et al. "Specific Detection of Non-Functional Human $P2X_7$ Receptors in HEK293 Cells and B-Lymphocytes" FEBS Letters (2003) 538: 159-162.
Gu B. J. ete al. "An $Arg^{307}$ to Gln Polymorphism Within the ATP-Binding Site Causes Loss of Function of Human $P2X_7$ Receptors" Journal of Biological Chemistry (2004) 279 (30) 31287-3195.
Wiley J. S. et al. "An Ile-568 to Asn Polymorphism Prevents Normal Trafficking and Function of the Human $P2X_7$ Receptor" Journal of Biological Chemistry (2003) 278 (19): 17108-17113.
U.S. Appl. No. 12/445,258, filed Apr. 10, 2009, Gidley-Baird et al.
Bird et al., "Single-Chain Antigen-Binding Proteins", *Science*, 242(4877):423-426, (1988).
Buell et al., "P2X Receptors: An Emerging Channel Family", *Eur J Neurosci*, 8:2221-2228, (1996).
Cheewatrakoolpong et al., "Identification and characterization of splice variants of the human $P2X_7$ ATP channel", *Biochem and Biophysical Res Comm*, 332:17-27, (2005).
Dangl et al., "Rapid Isolation of Cloned Isotype Switch Variants Using Fluorescence Activated Cell Sorting", Cytometry 2(6): 395-401, (1982).
Di Virgilio et al., "Responses of Mouse Lymphocytes to Extracellular Adenosine 5'-Triphosphate (ATP)", *J Immunology*, 143(6):1955-1960, (1989).
Dubyak et al, "Signal transduction via $P_2$-purinergic receptors for extracellular ATP and other nucleotides", *Am J Physiol*, 265(Cell Physiol. 34):C577-C606, (1993).
Feng et al., "A Truncated $P2X_7$ Receptor Variant ($P2X_{7-j}$) Endogenously Expressed in Cervical Cancer Cells Antagonizes the Full-length $P2X_7$ Receptor Through Hetero-oligomerization", *J Biol Chem*, 281(25):17228-17237, (2006).
Ferrari et al., "P2Z purinoreceptor ligation induces activation of caspases with distinct roles in apoptotic and necrotic alterations of cell death", *FEBS Letters*, 447:71-75, (1999).

(Continued)

*Primary Examiner* — Christine J Saoud
*Assistant Examiner* — Jon M Lockard
(74) *Attorney, Agent, or Firm* — Alston and Bird LLP

(57) ABSTRACT

The present invention relates to the production of anti non functional P2X7 receptor monoclonal antibodies from hybridoma cell lines.

11 Claims, 2 Drawing Sheets

OTHER PUBLICATIONS

Galfre et al., "Antibodies to major histocompatibility antigens produced by hybrid cell lines", *Nature*, 266:550-552, (1977).

Galfre et al., "Rat x rat hybrid myelomas and a monoclonal anti-Fd portion of mouse IgG", *Nature*, 277:131-133, (1979).

Gefter et al., "A Simple Method for Polyethylene Glycol-Promoted Hybridization of Mouse Myeloma Cells", *Somatic Cell Genetics*, 3(2):231-236, (1977).

Georgiou et al., "Human Epidermal and Monocyte-Derived Langerhans Cells Express Functional $P2X_7$ Receptors", *J Invest Dermatol*, 125:482-490. (2005).

Holliger et al., "'Diabodies'.: Small bivalent and bispecific antibody fragments", *Proc Natl Acad Sci*, 90:6444-6448, (1993).

Huston et al., "Protein engineering of antibody binding sites: Recovery of specific activity in an anti-digoxin single-chain Fv analogue produced in *Escherichia coli*", *Proc Natl Acad Sci*, 85:5879-5883, (1988).

Kim et al., "Differential Assembly of Rat Purinergic $P2X_7$ Receptor in Immune Cells of the Brain and Periphery", *J Biol Chem*, 276(26):23262-23267, (2001).

La Sala et al., "Alerting and tuning the immune response by extracellular nucleotides", *J Leukocyte Bio*, 73:339-343, (2003).

Poljak, "Production and structure of diabodies", *Structure*, 2:1121-1123, (1994).

Ralevic et al., "Receptors for Purines and Pyrimidines", *Pharm Rev*, 50(3):413-492, (1998).

Romagnoli et al., "Recent progress in the discovery of antagonists acting at $P2X_7$ receptor", *Expert Opin Ther Patents*, 15(3):271-287, (2005).

Slater et al., "Early prostate cancer detected using expression of non-functional cytolytic $P2X_7$ receptors", *Histopathology*, 44:206-215, (2004).

Slater et al., "Expression of the apoptotic calcium channel $P2X_7$ in the glandular epithelium is a marker for early prostate cancer and correlates with increasing PSA levels", *J Mol Hist*, 36:159-165, (2005).

Spieker-Polet et al., "Rabbit monoclonal antibodies: Generating a fusion partner to produce rabbit-rabbit hybridomas", *Proc Natl Acad Sci*, 92:9348-9352, (1995).

Surprenant et al., "The Cytolytic $P_{2z}$ Receptor for Extracellular ATP Identified as a $P_{2x}$ Receptor ($P2X_7$)", *Science*, 272:735-738, (1996).

Torres et al., "Hetero-oligomeric Assembly of P2X Receptor Subunits", *J Biol Chem*, 274(10):6653-6659, (1999).

Virginio et al., "Kinetics of cell lysis, dye uptake and permeability changes in cells expressing the rat $P2X_7$ receptor", *J Physiol*, 519(2):335-346, (1999).

Wang et al., "$P2X_7$ receptor-mediated apoptosis of human cervical epithelial cells", *Am J Physiol Cell Physiol*, 287:C1349-C1358, (2004).

Ward et al., "Binding activities of a repertoire of single immunoglobulin variable domains secreted from *Escherichia coli*", *Nature*, 341:544-546, (1989).

U.S. Appl. No. 12/878,865, filed May 12, 2011, Slater et al.
U.S. Appl. No. 12/975,341, filed Apr. 21, 2011, Barden et al.
U.S. Appl. No. 60/686,770, filed Jun. 2, 12005, Gorodeski et al.
U.S. Appl. No. 60/778,993, filed Mar. 3, 2006, Gorodeski et al.

Buell et al.,"Blockade of Human P2X7 Receptor Function With a Monoclonal Antibody," *Blood*, 92:3521-3528, (1998).

Burnstock et al., "P2 Purinergic Receptors: Modulation of Cell Function and Therapeutic Potential," *J Pharm Exp Therap*, 295:862-869, (2000).

Chessell et al., "Dynamics of P2X7 receptor pore dilation: pharmacological and functional consequences," *Drug Dev Res*, 53(2-3):60-65, (2001).

Di Virgiolio et al., "Purinergic P2X7 receptor: a pivotal role in inflammation and immunomodulation," *Drug Dev Res*, 45:207-213, (1998).

European Search Report of Apr. 1, 1997 for application EP96120926 (published as EP0781546).

European Search Report of Sep. 18, 2008 for application EP08156593 (published as EP1961767).

Feng et al., "ATP Stimulates GRK-3 phosphorylation and 3-arrestin-2-dependent internalization of P2X7 receptor," *Am J Physiol Cell Physiol*, 288:C1342-C1356, (2005).

Feng et al., "Endogenously Expressed Truncated P2X7 Receptor Lacking the C-Terminus is Preferentially Upregulated in Epithelial Cancer Cells and Fails to Mediate LigandInduced Pore Formation and Apoptosis, " *Nucleosides, Nucleotides and Nucleic Acids*, 25:1271-1276, (2006).

Ferrari et al., "ATP-mediated cytoxicity in microglial cells," *Neuropharmacology*, 36(9):1295-1301, (1997).

GenBank: Accession No. Y09561, versions Y09561.1, "H. sapiens mRNA for P2X7 receptor". [Retrieved from the Internet May 24, 2011: <URL: http://www.ncbi.nlm.nih.gov/nuccore/y09561>].

Greenbaum et al., "Comparing protein abundance and mRNA expression levels on a genomic scale," *Genome Biology*, 4(9):117.1-117.8, (2003).

Groschel-Stewart et al., "Localisation of P2X5 and P2X7 receptors by immunohistochemistry in rat *stratified squamous epithelia*," *Cell Tissue Res*, 296:599-605, (1999).

Gu et al, "A Glu-496 to Ala Polymorphism leads to loss of function of the human P2X7 receptor," *J Biol Chem*, 276(14):11135-11142, (2001).

Hansen et al., "Structural Motif and Characteristics of the Extracellular Domain of P2X Receptors," *Biochem and Biophys Res Comm*, 236(3):670-675, (1997).

Hansen et al., "The distribution of single P (2 x 1)—receptor clusters on smooth muscle cells in relation to nerve varicosities in the rat urinary bladder," *J Neurocytol*, 27(7): 529-539, (1998).

Hopfner et al, "Expression of functional P2-purinergic receptors in primary cultures of human colorectal carcinoma cells," *Biochem and Biophys Res Comm*, 251:811-817, (1998).

Jacob et al., "Cytogenetic Profile of Chronic Myeloid Leukemias," *Indian J Cancer*, 39(2):61-65, (2002).

Jameison et al., "Extracellular ATP causes loss of L-selectin from human lymphocytes via occupancy of P2Z purinoceptors," *J Cell Physiol*, 166:637-642 (1996).

Li et al., "P2X7 Receptor: A Novel Biomarker of Uterine Epithelial Cancers," *Cancer Epidemiol Biomarkers Prev*, 15(10):1906-1913, (2006).

Mager et al., "Prediction of the confirmation of the human P2X7 receptor," *Letts Drug Des Discov*, 3(10):675-682, (2006).

Mauro et al., "Chronic myelogenous leukaemia," *Curr Opin Oncol*, 13(1):3-7, (2001).

Meeker et al., "An additional breakpoint region in the BCL-1 locus associated with the t(11;14)(q13;q32) translocation of B-lymphocytic malignancy," *Blood*, 74:1801-1806, (1989).

Nawa et al., "Frequent loss of expression or aberrant alternative splicing of P2XM, a p53-inducible gene, in soft-tissue tumours," *Br J Cancer*, 80(8):1185-89, (1999).

Ngo et al "Computational complexity, protein structure prediction, and the Levinthal paradox," In Merz and Le Grand (eds), The protein folding problem and tertiary structure prediction, Birkhauser: Boston, pp. 491-495, (1994).

Nihei et al., "Pharmacologic properties of P2z/P2X7 receptor characterized in murine dendritic cells: role on the induction of apoptosis", *Blood*96(3)996-1005, (2000).

Paul, *Fundamental Immunology*, Lippincott Williams & Wilkins, p. 107, (1998).

PCT International Preliminary Examination Report of May 1, 2003 for application PCT/AU02/00061.

PCT International Preliminary Examination Report of Aug. 1, 2001 for application PCT/AU00/00363.

PCT International Preliminary Examination Report of Dec. 17, 2003 for application PCT/AU02/001204.

PCT International Preliminary Report on Patentability of Jan. 5, 2011 for application PCT/AU09/000869.

PCT International Preliminary Report on Patentability of Mar. 16, 2010 for application PCT/AU08/001364.

PCT International Preliminary Report on Patentability of Mar. 16, 2010 for application PCT/AU08/001365.

PCT International Preliminary Report on Patentability of Apr. 15, 2009 for application PCT/AU07/001540.

PCT International Preliminary Report on Patentability of Apr. 15, 2009 for application PCT/AU07/001541.

PCT International Search Report of Apr. 2, 2002 for application PCT/AU02/00061.

PCT International Search Report of Jul. 21, 2000 for application PCT/AU00/00363.
PCT International Search Report of Aug. 7, 2009 for application PCT/AU09/000869.
PCT International-Search Report of Sep. 22, 2010 for application PCT/AU10/001070.
PCT International Search Report of Oct. 14, 2002 for application PCT/AU02/001204.
PCT International Search Report of Oct. 27, 2008 for application PCT/AU08/001364.
PCT International Search Report of Nov. 9, 2007 for application PCT/AU07/001541.
PCT International Search Report of Nov. 21, 2008 for application PCT/AU08/001365.
PCT International Search Report of Nov. 2007 for application PCT/AU07/001540.
Peng et al., "P2Z purinoceptor, a special receptor for apoptosis induced by ATP in human leukemic lymphocytes," *Chinese Med J*, 112(4):356-362, (1999).
Programme and Abstract; 10th Symposium European Society for the Study of Purine and Pyrimidine Metabolism in Man, Jun. 8-11, 2005.
Rassendren et al., "The permeabilizing ATP receptor, P2X7: Cloning and expression of a human cDNA," *J Biol Chem*, 272(9):5482-5486, (1997).
Ray et al., "Purinergic receptor distribution in endothelial cells in blood vessels: a basis for selection of coronary artery grafts," *Atherosclerosis*, 162:55-61, (2002).
Slater et al., "Detection of preneoplasia in histologically normal prostate biopsies," *Prost Cancer Prostat Dis*, 4:92-96, (2001).
Slater et al., "Differentiation between cancerous and normal hyperplastic lobules in breast lesions," *Breast Cancer Res Treat*, 83:1-10, (2004).
Slater et al., "Increased expression of apoptotic markers in melanoma," *Melanoma Res*, 13(2):137-145. (2003).
Slater et al., "Markers for the development of early prostate cancer," *J Pathol*,199:368-377, (2003).
Sluyter et al., "Extracellular ATP increases cation fluxes in human erthrocytes by activation of the P2X7 receptor," *J Biol Chem*, 279(43):44749-44756, (2004).
Supplementary European Search Report of Mar. 4, 2011 for application EP01270623 (published as EP1352085).
Supplementary European Search Report of May 21, 2010 for application EP07815345 (published as EP2082032).
Supplementary European Search Report of Aug. 16, 2010 for application EP08800001 (published as EP2201377).
Supplementary European Search Report of Nov. 8, 2002 for application EP00918600 (published as EP1179183).
Supplementary Partial European Search Report of Apr. 29, 2005 for application EP02715313 (published as EP1360203).
Tockman et al., "Considerations in Bringing a Cancer Biomarker to Clinical Application," *Cancer Res*, 52:2711s-2718s, (1992).
U.S. Appl. No. 10/622,313 (now Patent No. 7,326,415), Non-Final Office Action mailed Nov. 30, 2006.
U.S. Appl. No. 10/622,313 (now Patent No. 7,326,415), Notice of Allowance and Examiner Interview Summary Record mailed Sep. 5, 2007.
U.S. Appl. No. 10/622,313 (now Patent No. 7,326,415), Requirement for Restriction/Election mailed Jun. 16, 2006.
U.S. Appl. No. 11/968,607 (now Patent No. 7,531,171), Non-Final Office Action mailed Sep. 26, 2008.
U.S. Appl. No. 11/968,607 (now Patent No. 7,531,171), Notice of Allowance mailed Jan. 9, 2009.
U.S. Appl. No. 11/968,607 (now Patent No. 7,531,171), Requirement for Restriction/Election mailed Aug. 19, 2008.
U.S. Appl. No. 12/417,989 (now Patent No. 7,888,473), Non-Final Office Action mailed Jun. 16, 2010.
U.S. Appl. No. 12/417,989 (now Patent No. 7,888,473), Notice of Allowance mailed Sep. 24, 2010.
U.S. Appl. No. 10/019,356 (now Patent No. 7,183,064), Final Office Action mailed May 9, 2006.
U.S. Appl. No. 10/019,356 (now Patent No. 7,183,064), Non-Final Office Action mailed Jul. 19, 2005.
U.S. Appl. No. 10/019,356 (now Patent No. 7,183,064), Notice of Allowance mailed Oct. 11, 2006.
U.S. Appl. No. 10/019,356 (now Patent No. 7,183,064), Requirement for Restriction/Election mailed Mar. 18, 2005.
U.S. Appl. No. 11/566,472, Examiner Interview Summary Record mailed Dec. 30, 2009.
U.S. Appl. No. 11/566,472, Final Office Action mailed Jan. 12, 2009.
U.S. Appl. No. 11/566,472, Final Office Action mailed Mar. 9, 2010.
U.S. Appl. No. 11/566,472, Non-Final Office Action mailed Jun. 16, 2008.
U.S. Appl. No. 11/566,472, Non-Final Office Action mailed Aug. 26, 2009.
U.S. Appl. No. 11/566,472, Requirement for Restriction/Election mailed Dec. 17, 2007.
U.S. Application No. 12/975,341, Non-Final Office Action mailed Mar. 24, 2011.
Urano et al., "Cloning of P2XM, a novel human P2X receptor gene regulated by p53," *Cancer Res*, 57:3281-87, (1997).
Von Kugelgen et al., "Molecular Pharmacology of P2Y-receptors," *Naunyn Scmiedebergs Arch Pharmacol*, 362:(4-5)310-323, (2000).
Vulchanova et al., "Immunohistochemical study of the P2X2 and P2X3 receptor subunits in rat and monkey sensory neurons and their central terminals," *Neuropharmacol*, 36(9):1229-1242, (1997).
Wells "Additivity of mutational effects in proteins," *Biochemistry*, 29(37):8509-8517, (1990).
Wiley et al., "A single nucleotide polymorphism is associated with loss of function of the monocyte P2X7 receptor," *Blood*, 96(11):17, (2000). Abstract.
Wiley et al., "Genetic polymorphisms of the human P2X7 receptor and relationship to function," *Drug Dev Res*, 53(2-3):72-76, (2001).
Williams et al., "Purinergic and pyrimidinergic receptors as potential drug targets," *Biochem Pharm*, 59:1173-1184, (2000).
Worthington et al., "Point mutations confer loss of ATP-induced human P2X7 receptor function," *FEBS Lett*, 512:43-46, (2002).
Wurl et al., "High prognostic significance of Mdm2/p53 co-overexpression in soft tissue sarcomas of the extremities," *Oncogene*,16(9):1183-85, (1998).

SEQUENCE LISTING

```
<160> NUMBER OF SEQ ID NOS: 8

<210> SEQ ID NO 1
<211> LENGTH: 595
<212> TYPE: PRT
<213> ORGANISM: Homo sapiens

<400> SEQUENCE: 1

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
```

```
                    20                  25                  30
Phe His Val Ile Ile Phe Ser Tyr Val Cys Phe Ala Leu Val Ser Asp
        35                  40                  45
Lys Leu Tyr Gln Arg Lys Glu Pro Val Ile Ser Ser Val His Thr Lys
        50                  55                  60
Val Lys Gly Ile Ala Glu Val Lys Glu Ile Val Glu Asn Gly Val
65                  70                  75                  80
Lys Lys Leu Val His Ser Val Phe Asp Thr Ala Asp Tyr Thr Phe Pro
                85                  90                  95
Leu Gln Gly Asn Ser Phe Phe Val Met Thr Asn Phe Leu Lys Thr Glu
                100                 105                 110
Gly Gln Glu Gln Arg Leu Cys Pro Glu Tyr Pro Thr Arg Arg Thr Leu
                115                 120                 125
Cys Ser Ser Asp Arg Gly Cys Lys Lys Gly Trp Met Asp Pro Gln Ser
        130                 135                 140
Lys Gly Ile Gln Thr Gly Arg Cys Val Val His Glu Gly Asn Gln Lys
145                 150                 155                 160
Thr Cys Glu Val Ser Ala Trp Cys Pro Ile Glu Ala Val Glu Glu Ala
                165                 170                 175
Pro Arg Pro Ala Leu Leu Asn Ser Ala Glu Asn Phe Thr Val Leu Ile
                180                 185                 190
Lys Asn Asn Ile Asp Phe Pro Gly His Asn Tyr Thr Thr Arg Asn Ile
                195                 200                 205
Leu Pro Gly Leu Asn Ile Thr Cys Thr Phe His Lys Thr Gln Asn Pro
                210                 215                 220
Gln Cys Pro Ile Phe Arg Leu Gly Asp Ile Phe Arg Glu Thr Gly Asp
225                 230                 235                 240
Asn Phe Ser Asp Val Ala Ile Gln Gly Gly Ile Met Gly Ile Glu Ile
                245                 250                 255
Tyr Trp Asp Cys Asn Leu Asp Arg Trp Phe His His Cys Arg Pro Lys
                260                 265                 270
Tyr Ser Phe Arg Arg Leu Asp Asp Lys Thr Thr Asn Val Ser Leu Tyr
        275                 280                 285
Pro Gly Tyr Asn Phe Arg Tyr Ala Lys Tyr Tyr Lys Glu Asn Asn Val
        290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asp Ile Ile Gln Leu Val Val Tyr
                325                 330                 335
Ile Gly Ser Thr Leu Ser Tyr Phe Gly Leu Ala Ala Val Phe Ile Asp
                340                 345                 350
Phe Leu Ile Asp Thr Tyr Ser Ser Asn Cys Cys Arg Ser His Ile Tyr
        355                 360                 365
Pro Trp Cys Lys Cys Cys Gln Pro Cys Val Val Asn Glu Tyr Tyr Tyr
        370                 375                 380
Arg Lys Lys Cys Glu Ser Ile Val Glu Pro Lys Pro Thr Leu Lys Tyr
385                 390                 395                 400
Val Ser Phe Val Asp Glu Ser His Ile Arg Met Val Asn Gln Gln Leu
                405                 410                 415
Leu Gly Arg Ser Leu Gln Asp Val Lys Gly Gln Glu Val Pro Arg Pro
                420                 425                 430
Ala Met Asp Phe Thr Asp Leu Ser Arg Leu Pro Leu Ala Leu His Asp
                435                 440                 445
```

```
Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 2
<211> LENGTH: 17
<212> TYPE: PRT
<213> ORGANISM: Homo sapiens

<400> SEQUENCE: 2

Gly His Asn Tyr Thr Thr Arg Asn Ile Leu Pro Gly Leu Asn Ile Thr
1               5                   10                  15

Cys

<210> SEQ ID NO 3
<211> LENGTH: 505
<212> TYPE: PRT
<213> ORGANISM: Homo sapiens

<400> SEQUENCE: 3

Met Thr Pro Gly Asp His Ser Trp Gly Asn Ser Phe Phe Val Met Thr
1               5                   10                  15

Asn Phe Leu Lys Thr Glu Gly Gln Glu Gln Arg Leu Cys Pro Glu Tyr
            20                  25                  30

Pro Thr Arg Arg Thr Leu Cys Ser Ser Asp Arg Gly Cys Lys Lys Gly
        35                  40                  45

Trp Met Asp Pro Gln Ser Lys Gly Ile Gln Thr Gly Arg Cys Val Val
50                  55                  60

His Glu Gly Asn Gln Lys Thr Cys Glu Val Ser Ala Trp Cys Pro Ile
65                  70                  75                  80

Glu Ala Val Glu Glu Ala Pro Arg Pro Ala Leu Leu Asn Ser Ala Glu
                85                  90                  95

Asn Phe Thr Val Leu Ile Lys Asn Asn Ile Asp Phe Pro Gly His Asn
            100                 105                 110

Tyr Thr Thr Arg Asn Ile Leu Pro Gly Leu Asn Ile Thr Cys Thr Phe
        115                 120                 125

His Lys Thr Gln Asn Pro Gln Cys Pro Ile Phe Arg Leu Gly Asp Ile
    130                 135                 140

Phe Arg Glu Thr Gly Asp Asn Phe Ser Asp Val Ala Ile Gln Gly Gly
145                 150                 155                 160
```

Ile Met Gly Ile Glu Ile Tyr Trp Asp Cys Asn Leu Asp Arg Trp Phe
               165                    170                175

His His Cys Arg Pro Lys Tyr Ser Phe Arg Leu Asp Asp Lys Thr
              180                 185               190

Thr Asn Val Ser Leu Tyr Pro Gly Tyr Asn Phe Arg Tyr Ala Lys Tyr
             195                   200                 205

Tyr Lys Glu Asn Asn Val Glu Lys Arg Thr Leu Ile Lys Val Phe Gly
    210                   215                 220

Ile Arg Phe Asp Ile Leu Val Phe Gly Thr Gly Lys Phe Asp Ile
225                  230                 235                240

Ile Gln Leu Val Val Tyr Ile Gly Ser Thr Leu Ser Tyr Phe Gly Leu
             245                   250              255

Ala Ala Val Phe Ile Asp Phe Leu Ile Asp Thr Tyr Ser Ser Asn Cys
             260                   265               270

Cys Arg Ser His Ile Tyr Pro Trp Cys Lys Cys Cys Gln Pro Cys Val
        275                   280               285

Val Asn Glu Tyr Tyr Arg Lys Lys Cys Glu Ser Ile Val Glu Pro
    290                   295               300

Lys Pro Thr Leu Lys Tyr Val Ser Phe Val Asp Glu Ser His Ile Arg
305                  310                 315                320

Met Val Asn Gln Gln Leu Leu Gly Arg Ser Leu Gln Asp Val Lys Gly
             325                   330              335

Gln Glu Val Pro Arg Pro Ala Met Asp Phe Thr Asp Leu Ser Arg Leu
             340                   345              350

Pro Leu Ala Leu His Asp Thr Pro Pro Ile Pro Gly Gln Pro Glu Glu
         355                   360                 365

Ile Gln Leu Leu Arg Lys Glu Ala Thr Pro Arg Ser Arg Asp Ser Pro
    370                   375                 380

Val Trp Cys Gln Cys Gly Ser Cys Leu Pro Ser Gln Leu Pro Glu Ser
385                  390                 395                400

His Arg Cys Leu Glu Glu Leu Cys Cys Arg Lys Lys Pro Gly Ala Cys
             405                   410              415

Ile Thr Thr Ser Glu Leu Phe Arg Lys Leu Val Leu Ser Arg His Val
             420                   425              430

Leu Gln Phe Leu Leu Leu Tyr Gln Glu Pro Leu Leu Ala Leu Asp Val
         435                   440                 445

Asp Ser Thr Asn Ser Arg Leu Arg His Cys Ala Tyr Arg Cys Tyr Ala
450                  455                 460

Thr Trp Arg Phe Gly Ser Gln Asp Met Ala Asp Phe Ala Ile Leu Pro
465                  470                 475                480

Ser Cys Cys Arg Trp Arg Ile Arg Lys Glu Phe Pro Lys Ser Glu Gly
             485                   490              495

Gln Tyr Ser Gly Phe Lys Ser Pro Tyr
         500                   505

<210> SEQ ID NO 4
<211> LENGTH: 425
<212> TYPE: PRT
<213> ORGANISM: Homo sapiens

<400> SEQUENCE: 4

Met Asp Gly Pro Ala Glu Gln Arg Pro Ala Leu Leu Asn Ser Ala Glu
1               5                 10                15

Asn Phe Thr Val Leu Ile Lys Asn Asn Ile Asp Phe Pro Gly His Asn
             20                   25               30

```
Tyr Thr Thr Arg Asn Ile Leu Pro Gly Leu Asn Ile Thr Cys Thr Phe
        35                  40                  45

His Lys Thr Gln Asn Pro Gln Cys Pro Ile Phe Arg Leu Gly Asp Ile
 50                  55                  60

Phe Arg Glu Thr Gly Asp Asn Phe Ser Asp Val Ala Ile Gln Gly Gly
 65                  70                  75                  80

Ile Met Gly Ile Glu Ile Tyr Trp Asp Cys Asn Leu Asp Arg Trp Phe
                 85                  90                  95

His His Cys Arg Pro Lys Tyr Ser Phe Arg Arg Leu Asp Asp Lys Thr
                100                 105                 110

Thr Asn Val Ser Leu Tyr Pro Gly Tyr Asn Phe Arg Tyr Ala Lys Tyr
            115                 120                 125

Tyr Lys Glu Asn Asn Val Glu Lys Arg Thr Leu Ile Lys Val Phe Gly
        130                 135                 140

Ile Arg Phe Asp Ile Leu Val Phe Gly Thr Gly Gly Lys Phe Asp Ile
145                 150                 155                 160

Ile Gln Leu Val Val Tyr Ile Gly Ser Thr Leu Ser Tyr Phe Gly Leu
                165                 170                 175

Ala Ala Val Phe Ile Asp Phe Leu Ile Asp Thr Tyr Ser Ser Asn Cys
                180                 185                 190

Cys Arg Ser His Ile Tyr Pro Trp Cys Lys Cys Gln Pro Cys Val
            195                 200                 205

Val Asn Glu Tyr Tyr Tyr Arg Lys Lys Cys Glu Ser Ile Val Glu Pro
        210                 215                 220

Lys Pro Thr Leu Lys Tyr Val Ser Phe Val Asp Glu Ser His Ile Arg
225                 230                 235                 240

Met Val Asn Gln Gln Leu Leu Gly Arg Ser Leu Gln Asp Val Lys Gly
                245                 250                 255

Gln Glu Val Pro Arg Pro Ala Met Asp Phe Thr Asp Leu Ser Arg Leu
            260                 265                 270

Pro Leu Ala Leu His Asp Thr Pro Ile Pro Gly Gln Pro Glu Glu
            275                 280                 285

Ile Gln Leu Leu Arg Lys Glu Ala Thr Pro Arg Ser Arg Asp Ser Pro
        290                 295                 300

Val Trp Cys Gln Cys Gly Ser Cys Leu Pro Ser Gln Leu Pro Glu Ser
305                 310                 315                 320

His Arg Cys Leu Glu Glu Leu Cys Cys Arg Lys Lys Pro Gly Ala Cys
                325                 330                 335

Ile Thr Thr Ser Glu Leu Phe Arg Lys Leu Val Leu Ser Arg His Val
            340                 345                 350

Leu Gln Phe Leu Leu Leu Tyr Gln Glu Pro Leu Leu Ala Leu Asp Val
                355                 360                 365

Asp Ser Thr Asn Ser Arg Leu Arg His Cys Ala Tyr Arg Cys Tyr Ala
        370                 375                 380

Thr Trp Arg Phe Gly Ser Gln Asp Met Ala Asp Phe Ala Ile Leu Pro
385                 390                 395                 400

Ser Cys Cys Arg Trp Arg Ile Arg Lys Glu Phe Pro Lys Ser Glu Gly
                405                 410                 415

Gln Tyr Ser Gly Phe Lys Ser Pro Tyr
                420                 425

<210> SEQ ID NO 5
<211> LENGTH: 354
<212> TYPE: PRT
```

<213> ORGANISM: Homo sapiens

<400> SEQUENCE: 5

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Val Arg Asp Ser Glu Gly
            340                 345                 350

Ser Asp

<210> SEQ ID NO 6
<211> LENGTH: 306
<212> TYPE: PRT
<213> ORGANISM: Homo sapiens

<400> SEQUENCE: 6

Met Trp Gln Phe Arg Tyr Ala Lys Tyr Tyr Lys Glu Asn Asn Val Glu
1               5                   10                  15

Lys Arg Thr Leu Ile Lys Val Phe Gly Ile Arg Phe Asp Ile Leu Val
                20                  25                  30

Phe Gly Thr Gly Gly Lys Phe Asp Ile Ile Gln Leu Val Val Tyr Ile
            35                  40                  45

Gly Ser Thr Leu Ser Tyr Phe Gly Leu Ala Ala Val Phe Ile Asp Phe
50                  55                  60

Leu Ile Asp Thr Tyr Ser Ser Asn Cys Cys Arg Ser His Ile Tyr Pro
65                  70                  75                  80

Trp Cys Lys Cys Cys Gln Pro Cys Val Val Asn Glu Tyr Tyr Arg
                85                  90                  95

Lys Lys Cys Glu Ser Ile Val Glu Pro Lys Pro Thr Leu Lys Tyr Val
                100                 105                 110

Ser Phe Val Asp Glu Ser His Ile Arg Met Val Asn Gln Gln Leu Leu
            115                 120                 125

Gly Arg Ser Leu Gln Asp Val Lys Gly Gln Glu Val Pro Arg Pro Ala
        130                 135                 140

Met Asp Phe Thr Asp Leu Ser Arg Leu Pro Leu Ala Leu His Asp Thr
145                 150                 155                 160

Pro Pro Ile Pro Gly Gln Pro Glu Glu Ile Gln Leu Leu Arg Lys Glu
                165                 170                 175

Ala Thr Pro Arg Ser Arg Asp Ser Pro Val Trp Cys Gln Cys Gly Ser
            180                 185                 190

Cys Leu Pro Ser Gln Leu Pro Glu Ser His Arg Cys Leu Glu Glu Leu
        195                 200                 205

Cys Cys Arg Lys Lys Pro Gly Ala Cys Ile Thr Thr Ser Glu Leu Phe
210                 215                 220

Arg Lys Leu Val Leu Ser Arg His Val Leu Gln Phe Leu Leu Leu Tyr
225                 230                 235                 240

Gln Glu Pro Leu Leu Ala Leu Asp Val Asp Ser Thr Asn Ser Arg Leu
                245                 250                 255

Arg His Cys Ala Tyr Arg Cys Tyr Ala Thr Trp Arg Phe Gly Ser Gln
            260                 265                 270

Asp Met Ala Asp Phe Ala Ile Leu Pro Ser Cys Cys Arg Trp Arg Ile
        275                 280                 285

Arg Lys Glu Phe Pro Lys Ser Glu Gly Gln Tyr Ser Gly Phe Lys Ser
    290                 295                 300

Pro Tyr
305

<210> SEQ ID NO 7
<211> LENGTH: 275
<212> TYPE: PRT
<213> ORGANISM: Homo sapiens

<400> SEQUENCE: 7

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
                20                  25                  30

Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
50                  55                  60

-continued

Val Lys Gly Ile Ala Glu Val Lys Glu Glu Ile Val Glu Asn Gly Val
 65                  70                  75                  80

Lys Lys Leu Val His Ser Val Phe Asp Thr Ala Asp Tyr Thr Phe Pro
                 85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Gly Trp Met Asp Pro Gln Ser
130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Tyr Ala Lys
        195                 200                 205

Tyr Tyr Lys Glu Asn Asn Val Glu Lys Arg Thr Leu Ile Lys Val Phe
210                 215                 220

Gly Ile Arg Phe Asp Ile Leu Val Phe Gly Thr Gly Gly Lys Phe Asp
225                 230                 235                 240

Ile Ile Gln Leu Val Val Tyr Ile Gly Ser Thr Leu Ser Tyr Phe Gly
                245                 250                 255

Leu Val Arg Asp Ser Leu Phe His Ala Leu Gly Lys Trp Phe Gly Glu
            260                 265                 270

Gly Ser Asp
        275

<210> SEQ ID NO 8
<211> LENGTH: 274
<212> TYPE: PRT
<213> ORGANISM: Homo sapiens

<400> SEQUENCE: 8

Met Thr Pro Gly Asp His Ser Trp Gly Asn Ser Phe Phe Val Met Thr
 1               5                  10                  15

Asn Phe Leu Lys Thr Glu Gly Gln Glu Gln Arg Leu Cys Pro Glu Tyr
                20                  25                  30

Pro Thr Arg Arg Thr Leu Cys Ser Ser Asp Arg Gly Cys Lys Lys Gly
            35                  40                  45

Trp Met Asp Pro Gln Ser Lys Gly Ile Gln Thr Gly Arg Cys Val Val
 50                  55                  60

His Glu Gly Asn Gln Lys Thr Cys Glu Val Ser Ala Trp Cys Pro Ile
 65                  70                  75                  80

Glu Ala Val Glu Glu Ala Pro Arg Pro Ala Leu Leu Asn Ser Ala Glu
                 85                  90                  95

Asn Phe Thr Val Leu Ile Lys Asn Asn Ile Asp Phe Pro Gly His Asn
            100                 105                 110

Tyr Thr Thr Arg Asn Ile Leu Pro Gly Leu Asn Ile Thr Cys Thr Phe
        115                 120                 125

His Lys Thr Gln Asn Pro Gln Cys Pro Ile Phe Arg Leu Gly Asp Ile
130                 135                 140

Phe Arg Glu Thr Gly Asp Asn Phe Ser Asp Val Ala Ile Gln Gly Gly
145                 150                 155                 160

```
Ile Met Gly Ile Glu Ile Tyr Trp Asp Cys Asn Leu Asp Arg Trp Phe
            165             170                 175

His His Cys Arg Pro Lys Tyr Ser Phe Arg Arg Leu Asp Asp Lys Thr
            180             185                 190

Thr Asn Val Ser Leu Tyr Pro Gly Tyr Asn Phe Arg Tyr Ala Lys Tyr
        195             200                 205

Tyr Lys Glu Asn Asn Val Glu Lys Arg Thr Leu Ile Lys Val Phe Gly
    210             215             220

Ile Arg Phe Asp Ile Leu Val Phe Gly Thr Gly Gly Lys Phe Asp Ile
225             230             235                 240

Ile Gln Leu Val Val Tyr Ile Gly Ser Thr Leu Ser Tyr Phe Gly Leu
            245             250                 255

Val Arg Asp Ser Leu Phe His Ala Leu Gly Lys Trp Phe Gly Glu Gly
            260             265                 270

Ser Asp
```

HYBRIDOMAS PRODUCING ANTIBODIES AGAINST NON FUNCTIONAL P2X7 RECEPTOR

CROSS-REFERENCE TO RELATED APPLICATIONS

The present application is the U.S. National Phase entry under 35 U.S.C. §371 of International Application No. PCT/AU2007/001540, filed Oct. 10, 2007, which claims the benefit under 35 U.S.C. §119(a) of Australian Application No. 2006905591, filed on Oct. 10, 2006.

REFERENCE TO A "SEQUENCE LISTING," A TABLE, OR A COMPUTER PROGRAM LISTING SUBMITTED IN COMPUTER READABLE FORMAT

The Sequence Listing written in the file 027281-000700US_SEQ.txt is 24,251 bytes bytes, and was created on Apr. 10, 2009, for the application filed herewith, Barden et al. "HYBRIDOMAS PRODUCING ANTIBODIES AGAINST NON FUNCTIONAL P2X7 RECEPTOR." The information contained in this file is hereby incorporated by reference.

FIELD OF THE INVENTION

The present invention relates to the production of monoclonal antibodies from hybridoma cell lines.

BACKGROUND OF THE INVENTION

Purinergic (P2X) receptors are ATP-gated cation-selective channels. Each receptor is made up of three protein subunits or monomers. To date seven separate genes encoding P2X monomers have been identified: P2X1, P2X2, P2X3, P2X4, P2X5, P2X6, P2X7.

P2X7 receptors are of particular interest as the expression of these receptors is understood to be limited to cells having potential to undergo programmed cell death, such as thymocytes, dendritic cells, lymphocytes, macrophages and monocytes. There is some expression of P2X7 receptors in normal homeostasis, such as on erythrocytes.

Interestingly, a P2X7 receptor containing one or more monomers having a cis isomerisation at Pro210 (SEQ ID NO: 1) and which is devoid of ATP binding function has been found on cells that are understood to be unable to undergo programmed cell death, such as preneoplastic cells and neoplastic cells. This isoform of the receptor has been referred to as a "non functional" receptor.

Antibodies generated from immunisation with a peptide including Pro210 in cis bind to non functional P2X7 receptors. However, they do not bind to P2X7 receptors capable of binding ATP. Accordingly, these antibodies are useful for selectively detecting many forms of carcinoma and haemopoietic cancers and to treatment of some of these conditions.

WO02/057306A1 and WO03/020762A1 both discuss a probe for distinguishing between functional P2X7 receptors and non functional P2X7 receptors in the form of a monoclonal antibody.

To date it has been very difficult to obtain a hybridoma that generates useful amounts of antiserum against non functional P2X7 receptors, and in particular, antiserum that can be used in a range of diagnostic and therapeutic applications. Indeed, apart from the hybridomas and antibodies forming part of this invention, the Applicant is unaware of any other hybridomas or monoclonal antibodies against anti-non functional P2X7 receptors that could be robustly used in applications to detect or treat cancer and other conditions associated with non functional P2X7 receptor expression.

SUMMARY OF THE INVENTION

In one embodiment there is provided a hybridoma for producing an antibody that is capable of forming an immune complex with a non functional P2X7 receptor, the hybridoma being characterised in that it produces an antibody that has an affinity for non functional P2X7 receptors expressed on a live cell of less than about $5 \times 10^6$ $M^{-1}$.

In another embodiment there is provided an antibody produced by a hybridoma described above.

In other embodiments there is provided a fragment of a monoclonal antibody described above that is capable of forming an immune complex with a non functional P2X7 receptor.

In other embodiments there is provided an immune complex formed from the binding of an antibody or fragment described above to a non functional P2X7 receptor, monomer or fragment thereof, or to a peptide having a sequence shown in SEQ ID NO:2.

In certain embodiments there is provided a method for determining whether a cell, tissue or extra cellular body fluid includes a non functional P2X7 receptor, monomer or fragment thereof including:
  contacting a cell, tissue or extra cellular body fluid with an antibody or fragment described above in conditions for forming an immune complex as described above, and
  detecting whether an immune complex has been formed,
  wherein detection of an immune complex determines that a cell, tissue or extra-cellular body fluid includes a non functional P2X7 receptor, monomer or fragment thereof.

In yet further embodiments there is provided a kit or composition for determining whether a cell, tissue or extra-cellular body fluid contains a non functional P2X7 receptor, monomer or fragment thereof including:
  an antibody or fragment described above and optionally;
  a further antibody for binding to the antibody or fragment or the non functional P2X7 receptor, monomer or fragment thereof;
  written instructions for use of the kit in a method described above.

In other embodiments there is provided a pharmaceutical composition including an antibody or fragment as described above together with a pharmaceutically acceptable carrier, diluent or excipient.

In related embodiments there is provided a method of treatment of a disease characterised by the expression of a non ATP-binding P2X7 receptor, monomer or fragment thereof including the step of providing an antibody or fragment thereof as described above, or a peptide as described above to an individual requiring said treatment.

DETAILED DESCRIPTION OF THE INVENTION

Figure 1:
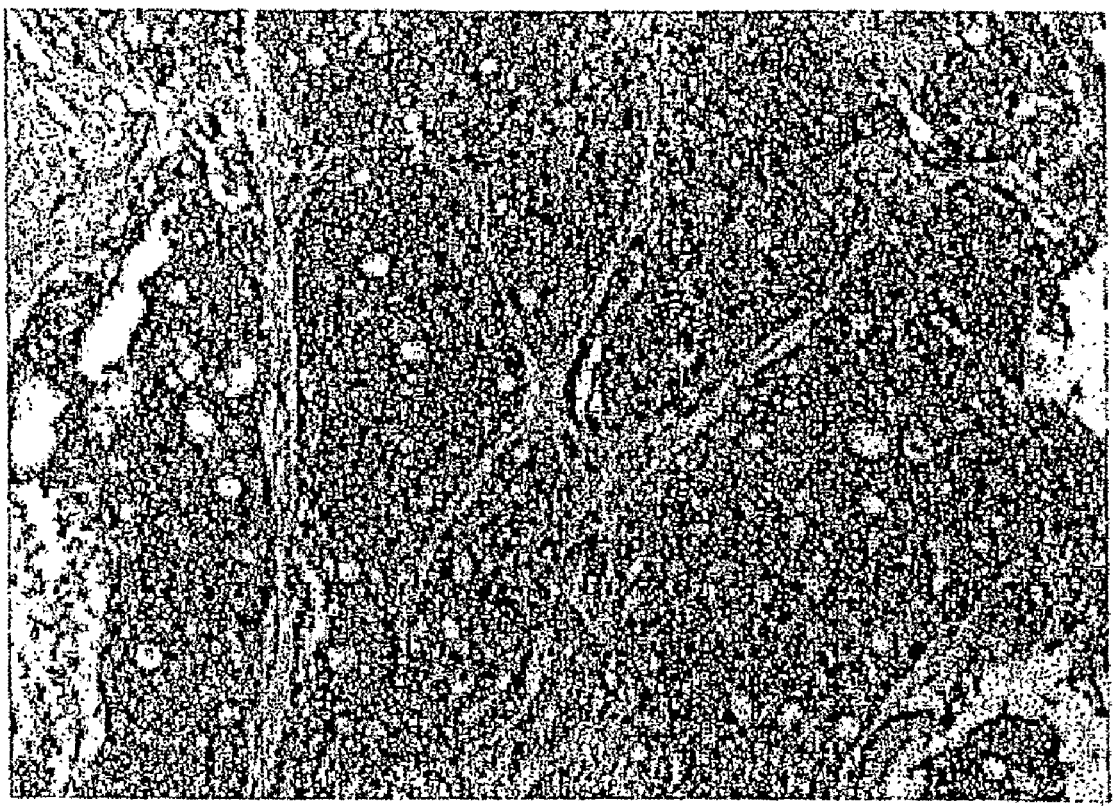
FIG. 1 shows BPM09 immunohistochemical staining of human prostate cancer tissue.

The anti P2X7 antisera against non functional P2X7 receptors available at the time of the invention have all been polyclonal. Apart from the Applicant's own work, no anti-non functional P2X7 receptor monoclonal antibodies have been made.

The inventors have attempted to obtain anti non functional P2X7 receptor monoclonal antibodies using techniques for monoclonal antibody production known in the art. In accordance with conventional techniques, a key step in this process has been to screen and to select for hybridomas for antibody production that produce supernatants having high affinity for the peptide immunogen against which they have been raised (Goding James W. Monoclonal antibodies: principles and practice: production and application of monoclonal antibodies in cell biology, biochemistry and immunology.—2nd ed. 1986 Academic Press, Harcour Brace Jovnovich, Publishers).

In forming this invention, the inventors found that these techniques tend to result in hybridomas that exhibit poor growth in mice and that are sensitive to cell culture techniques including passaging, freezing, thawing and seeding. Consequently the inventors have found it to be very difficult to generate useful amounts of antibody from hybridomas selected according to the conventional monoclonal antibody production techniques.

Further, the inventors have found that the hybridomas selected for antibody production on the basis of high affinity binding to peptide immunogen tend to produce antibodies that also have high affinity for non functional P2X7 receptors expressed on the surface of live cells. The inventors now believe that these antibodies bind to the hybridomas that produce them with high affinity.

Still further, in forming this invention the inventors have screened for hybridomas that secrete antibodies that bind to non functional P2X7 receptors expressed on live cells with low affinity, and then determined the capacity of these hybridoma cells to grow in mice and tissue culture. The inventors have surprisingly found that the hybridomas showed a much better potential for growth and stability than those that secrete antibodies that bind to receptors on live cells with high affinity. As a result, the inventors have been able to produce large amounts of monoclonal antibody to non functional P2X7 receptors.

Further, the inventors have surprisingly found that the antibodies having a low affinity for non functional receptors expressed on live cells have a high affinity for non functional receptors expressed on dead or fixed cells or tissues, such as fixed cells that are routinely screened in FACS and paraffin tissue sections. Accordingly, the inventors have been able to produce large amounts of monoclonal antibody useful in a wide range of diagnostic applications not involving live cells, such as FACS, histology and various other cell-free serological applications including ELISA, RIA and the like.

Thus, in one embodiment there is provided a hybridoma for producing an antibody that is capable of forming an immune complex with a non functional P2X7 receptor, the hybridoma being characterised in that it produces an antibody that has an affinity for non functional P2X7 receptors expressed on a live cell of less than about $5 \times 10^6$ $M^{-1}$, preferably less than about $5 \times 10^5$ $M^{-1}$, more preferably about $5 \times 10^4$ $M^{-1}$ or less, or in the range of from $5 \times 10^4$ $M^{-1}$ to $5 \times 10^5$ $M^{-1}$. In one embodiment, the hybridoma is characterised in that it produces an antibody that has an affinity that is about the same as the affinity of antibody BPM09 disclosed herein for a non functional receptor expressed on a live cell. An example of a live cell is a myeloma or hybridoma cell. Other live cells or cell lines include those expressing non functional P2X7 receptor, such as prostate PC3.

One example of a hybridoma according to this embodiment of the invention is hybridoma AB253 deposited with the European Collection of Cell Cultures (ECACC) under Accession no. 06080101. The inventors have found that this hybridoma is stable in the sense that it grows and consistently produces antiserum against non function P2X7 receptors after passaging and freeze/thawing. Thus in one embodiment there is provided hybridoma AB253 deposited with the European Collection of Cell Cultures (ECACC) under Accession no. 06080101. A sample of the hybridoma AB253 was deposited with (ECACC), Porton Down, Salisbury, Wiltshire, SP4 0JG, United Kingdom, on 1 Aug. 2006.

In another embodiment there is provided an antibody produced by a hybridoma described above. Monoclonal antibody BPM09, which is produced by the hybridoma AB253 deposited with the European Collection of Cell Cultures (ECACC) under Accession no. 06080101 is an example of a monoclonal antibody according to this embodiment. This antibody is distinguished from other tumour-selective $P2X_7$ polysera, in particular in respect to its superior immunohistochemical staining of tumour tissue. Labelled BPM09 antibodies bind strongly to tumour tissue, with minimal staining of normal tissue, when compared to other anti-$P2X_7$ tumour selective polyclonal antibodies.

In further embodiments, a monoclonal antibody produced by a hybridoma of the invention is one which is raised against a peptide having a sequence shown in SEQ ID NO: 2. Examples include the following monoclonal antibodies: BPM01, BPM02, BPM03, BPM04, BPM05, BPM06, BPM07, BPM08, BPM10, also further described herein. In other embodiments, a monoclonal antibody produced by a hybridoma of the invention is one which is raised against a peptide derived from elsewhere in the extracellular domain or other domain of a non functional P2X7 receptor.

As known in the art, an "antibody" is an immunoglobulin molecule. Five isotypes are known: IgG, IgA, IgM, IgD and IgE. All antibodies (except for IgM) are comprised of four polypeptide chains in the form of two heavy (H) chains and two light (L) chains inter-connected by disulfide bonds. Each heavy chain is comprised of a heavy chain variable region (HCVR or $V_H$) and a heavy chain constant region. The heavy chain constant region comprises three domains, $C_H1$, $C_H2$ and $C_H3$. Each light chain is comprised of a light chain variable region (LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. IgM has the above structure, however it is pentameric. In one embodiment, the monoclonal antibody is an IgG1 isotype.

The term "domain" as used herein is meant a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain.

The term "variable domain" as used herein is meant a folded polypeptide domain comprising sequences characteristic of immunoglobulin heavy or light chain variable domains and which specifically binds an antigen.

The term "immunoglobulin" as used herein refers to a family of polypeptides which retain the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor).

In other embodiments there is provided a fragment of a monoclonal antibody described above that is capable of forming an immune complex with non functional P2X7 receptor. These fragments are typically formed by a chemical reaction or modification of a monoclonal antibody. One example is a Fab fragment which is formed by papain digestion of whole antibody. The fragments typically retain the same affinity for antigen as the whole antibody from which they are derived.

The antibody or fragment may be provided on a solid phase such as a bead, surface or tissue culture vessel.

The antibody or fragment may be provided with a label for detection of binding of the antibody or fragment to antigen.

The antibodies and fragments may be labelled for use in medical imaging. Such methods involve chemical attachment of a labelling or imaging agent, such as a radioisotope, which include 67 Cu, 90 Y, 125 I, 131 I, 186 Re, 188Re, 211 At, 212 Bi, administration of the labelled antibody or fragment to a subject in an acceptable carrier, and imaging the labelled antibody or fragment in vivo at the target site. Radio-labelled antibodies or fragments thereof may be particularly useful in in vivo imaging of cancers described herein.

The antibodies can be purified by methods known to the skilled artisan. Purification methods include, among other, selective precipitation, liquid chromatography, HPLC, electrophoresis, chromatofocusing, and various affinity techniques.

In some embodiments, the antibodies disclosed herein may also include multimeric forms of antibodies. For example, antibodies of the invention may take the form of antibody dimers, trimers, or higher-order multimers of monomeric immunoglobulin molecules.

Crosslinking of antibodies can be done through various methods known in the art. For example, crosslinking of antibodies may be accomplished through natural aggregation of antibodies, through chemical or recombinant linking techniques or other methods known in the art. For example, purified antibody preparations can spontaneously form protein aggregates containing antibody homodimers, and other higher-order antibody multimers. In a specific embodiment, crosslinking of antibodies by using a second antibody to bind to the antibodies of interest can be used to form a homodimer. The crosslinker antibody can be derived from a different animal compared to the antibody of interest. For example, a goat anti-mouse antibody (Fab specific) may be added to a mouse monoclonal antibody to form a homodimer. This bivalent crosslinker antibody recognizes the Fab or Fc region of the two antibodies of interest forming a homodimer.

Alternatively, antibody homodimers may be formed through chemical linkage techniques known in the art. Chemical crosslinkers can be homo or heterobifunctional and will covalently bind with two antibodies forming a homodimer. In some embodiments, it is desirable that the chemical crosslinker not interact with the antigen-binding region of the antibody as this may affect antibody function. As will be appreciated by those skilled in the art, antibodies can be crosslinked at the Fab region.

In other embodiments there is provided an immune complex formed from the binding of an antibody or fragment described above to a non functional P2X7 receptor, monomer or fragment thereof, or to a peptide shown in SEQ ID NO 2.

The immune complex, otherwise known as an antibody-antigen complex, or a complex formed from the binding of an antigen binding site of an antibody or fragment thereof to an antigenic determinant or epitope, is particularly important as detection of this in vitro or in vivo is indicative of presence of, or predisposition to a disease or condition including preneoplasia and neoplasia. These detection methods are described in more detail below.

The P2X7 receptor, monomer or fragment thereof included in the immune complex may have Pro210 in cis isomerisation.

The P2X7 receptor, monomer or fragment thereof included in the immune complex may have an amino acid sequence as shown in any one of SEQ ID NO:s. 3 to 8 or fragment thereof.

The P2X7 receptor, monomer or fragment thereof included in the immune complex may have a molecular weight in the range of from about 15 to 80 kDa, not including the molecular weight of the antibody or antibody fragment. The total molecular weight depends on whether the complex is formed from a whole antibody or fragment thereof.

The P2X7 receptor, monomer or fragment thereof included in the immune complex may lack a transmembrane domain.

The immune complex may be formed by binding a P2X7 receptor, monomer or fragment thereof located on a cell surface membrane, in a cytoplasm, in a nucleus or in extra-cellular fluid. The extra-cellular fluid may be blood, plasma, serum, lymph, urine, semen, saliva, sputum, ascites, faeces, uterine and vaginal secretions, bile, amniotic fluid, cerebrospinal fluid and organ and tissue flushings.

The antibody or antibody fragment included in the immune complex may be attached to a solid phase, such as a bead or a plate, so that the immune complex is attached to a solid phase when formed. Alternatively, the P2X7 receptor, monomer or fragment thereof included in the immune complex may be attached to a solid phase.

The antibody may be labelled for detection of formation of the immune complex.

The immune complex may further include an antibody or fragment thereof, such as a capture antibody for capture of the immune complex. The further antibody or fragment thereof may bind to the anti P2X7 receptor antibody. Also, the further antibody or fragment thereof may bind to the receptor or fragment thereof.

The further antibody or fragment thereof may be bound to a solid phase such as a phase described above.

The further antibody may be labelled for detection of formation of the immune complex. Examples of labels include fluorophores, dyes, isotopes etc.

In certain embodiments there is provided a method for determining whether a cell, tissue or extra cellular body fluid includes a non functional P2X7 receptor, monomer or fragment thereof including:

contacting a cell, tissue or extra cellular body fluid with an antibody or fragment described above in conditions for forming an immune complex as described above, and detecting whether an immune complex has been formed, wherein detection of an immune complex determines that a cell, tissue or extra-cellular body fluid includes a non functional P2X7 receptor, monomer or fragment thereof.

In other embodiments there is provided a use of an antibody or fragment thereof described above in the manufacture of means for determining whether a cell, tissue or extra-cellular body fluid contains a P2X7 receptor, monomer or fragment thereof.

The presence of a given protein, or level of expression of a given protein in a host cell, tissue or extra-cellular body fluid can be detected by any number of assays. Examples include immunoassays, chromatography and mass spectrometry.

Immunoassays, i.e. assays involving an element of the immune system are particularly preferred. These assays may generally be classified into one of:

(i) assays in which purified antigen is used to detect an antibody in host serum. For example, purified antigen is bound to solid phase by adsorption or indirectly through another molecule and host serum is applied followed by another antibody for detecting presence or absence of host antibody;

(ii) assays in which purified antigen is used to detect immune cells, such as T and B lymphocytes. For example, peripheral white cells are purified from a host and cultured with purified antigen. The presence or absence of one or factors indicating immunity are then detected. Other examples include assays that measure cell proliferation (lymphocyte proliferation or transformation assays) following exposure to purified antigen, and assays that measure cell death (including apoptosis) following exposure to purified antigen;

(iii) assays in which purified antibody specific for antigen is used to detect antigen in the host. For example, purified antibody is bound to solid phase, host tissue is then applied followed by another antibody specific for the antigen to be detected. There are many examples of this approach including ELISA, RIA;

(iv) assays in which a purified anti-idiotypic antibody is used to detect host antibody. For example, anti-idiotypic antibody is adsorbed to solid phase, host serum is added and anti-Fc antibody is added to bind to any host antibodies having been bound by the anti-idiotypic antibody.

The immunoassays can be applied in vitro or in vivo.

In one embodiment, the disease is typically a cancer such as carcinoma, sarcoma, lymphoma, or leukemia. Carcinomas that may be detected include, but not limited to, prostate, breast, skin, lung, cervix, uterus, stomach, oesophagus, bladder, and colon cancers.

Whilst any body fluid can be used to detect any of these diseases, some body fluids may be more appropriate than others to detect certain diseases, for example urine may be more appropriate to detect prostate cancer and blood for detecting blood cancers such as lymphoma.

In certain embodiments, cancer is selected from the group consisting of prostate cancer, invasive breast cancer, melanoma, adenocarcinoma of the bowel, serous ovarian cancer, squamous cell cancer of the cervix, endometrial cancer, small cell lung cancer, hepatocellular carcinoma, transitional cell carcinoma of the bladder, gastrointestinal stromal tumour, endometrial stromal tumour, pituitary cancer, mesothelioma, Hodgkin's lymphoma and thyroid papillary.

In yet further embodiments there is provided a kit or composition for determining whether a cell, tissue or extra-cellular body fluid contains a non functional P2X7 receptor, monomer or fragment thereof including:

an antibody or fragment described above and optionally;
a further antibody for binding to the antibody or fragment or the non functional P2X7 receptor, monomer or fragment thereof;
written instructions for use of the kit in a method described above.

Kits are provided which contain the necessary reagents to carry out the assays of the present invention. The kit may include one or more compartments, each to receive one or, more containers such as: (a) a first container comprising one of the components of the present invention described above; and (b) one or more other containers comprising one or more of the following: wash reagents, reagents capable of detecting presence of the antibody or peptide.

The containers allow one to efficiently transfer reagents from one compartment to another compartment such that the samples and reagents are not cross-contaminated, and the agents or solutions of each container can be added in a quantitative fashion from one compartment to another.

The kit typically contains containers which may be formed from a variety of materials such as glass or plastic, and can include for example, bottles, vials, syringes, and test tubes. A label typically accompanies the kit, and includes any writing or recorded material, which may be electronic or computer readable form (e.g., disk, optical disc, or tape) providing instructions or other information for used of the contents of the kit. The label indicates that the formulation is used for diagnosing or treating the disorder of choice.

One skilled in the art will readily recognize that the disclosed antibodies and peptides of the present invention can be readily incorporated into one of the established kit formats which are well known in the art.

In other embodiments there is provided a pharmaceutical composition including an antibody or fragment as described above together with a pharmaceutically acceptable carrier, diluent or excipient.

In the preparation of the pharmaceutical compositions comprising the antibodies or peptides described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the antibodies or peptides, or mixture of antibodies or mixture of peptides, or suitable salts thereof.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies and peptides is intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions will often further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

While any suitable carrier known to those of ordinary skill in the art may be employed in the compositions of this invention, the type of carrier will typically vary depending on the mode of administration. Antibody and peptide compositions may be formulated for any appropriate manner of administration, including for example, oral, nasal, mucosal, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies and peptides can be administered in the form of a depot injection or implant preparation which can be formulated in such a manner as to permit a sustained release of the active ingredient. An exemplary composition comprises antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions; solid or powder forms suitable for reconstitution with suitable vehicles, including by way example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a freeze-dried condition requiring only the addition of a sterile liquid carrier immediately prior to use.

In related embodiments there is provided a method of treatment of a disease characterised by the expression of a non ATP-binding P2X7 receptor, monomer or fragment thereof including the step of providing an antibody or fragment thereof as described above, or a peptide as described above to an individual requiring said treatment.

Methods of immunotargeting cancer cells using antibodies or antibody fragments are well known in the art. U.S. Pat. No. 6,306,393 describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include complement-mediated cytolysis, antibody-dependent cellular cytotoxicity (ADCC)1 modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The antibodies can also be conjugated to toxic or therapeutic agents, such as radioligands or cytosolic toxins, and may also be used therapeutically to deliver the toxic or therapeutic agent directly to tumor cells.

By "treatment" herein is meant therapeutic or prophylactic treatment, or a suppressive measure for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

The therapeutic preparations can use nonmodified antibodies or antibodies conjugated with a therapeutic compound, such as a toxin or cytotoxic molecule, depending on the functionality of the antibody. Generally, when nonmodified antibodies are used, they will typically have a functional Fc region. By "functional Fc region" herein is meant a minimal sequence for effecting the biological function of Fc, such as binding to Fc receptors, particularly FcγR (e.g., Fcγ RI, FcγRII, and Fcγ RIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonals will be advantageous because they will bind to different epitopes and thus have a higher density of Fc on the cell surface as compared to when a single monoclonal antibody is used. Of course, to enhance their effectiveness in depleting targeted cells, or where nonmodified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific. For example, for treating chronic myeloid leukemia arising from BCR-ABL activity, one class of useful compounds are inhibitors of abl kinase activity, such as Imatinib, an inhibitor of bcr-abl kinase, and antisense oligonucleotides against bcr (e.g., Oblimersen). Other agents include, among others, interferon-alpha, humanized anti-CD52, deacetylase inhibitor FR901228 (depsipeptide), and the like.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from prostate cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease. Determining the dosages and times of administration for a therapeutically effective amount are well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al., Semin. Oncol. 26.suppl. 12) 60-70 (1999) describes in vitro measurements of antibody dependent cellular cytoxicity. A dose can then be formulated in animal models to generate a circulating concentration or tissue concentration, including that of the IC50 as determined by the cell culture assays.

In addition, the toxicity and therapeutic efficacy are generally determined by cell culture assays and/or experimental animals, typically by determining a LD50 (lethal dose to 50% of the test population) and ED50 (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences such as, for example, in the case of a chimeric or humanized antibody. Within certain embodiments, an initial high dose of antibody is administered such that a degree of immunological tolerance to the therapeutic antibody is established.

The tolerizing dose is sufficient to prevent or reduce the induction of an antibody response to repeat administration of the committed progenitor cell specific antibody.

Preferred ranges for the tolerizing dose are between 10 mg/kg body weight to 50 mg/kg body weight, inclusive. More preferred ranges for the tolerizing dose are between 20 and 40 mg/kg, inclusive. Still more preferred ranges for the tolerizing dose are between 20 and 25 mg/kg, inclusive.

Within these therapeutic regimens, the therapeutically effective dose of antibodies is preferably administered in the range of 0.1 to 10 mg/kg body weight, inclusive. More preferred second therapeutically effective doses are in the range of 0.2 to 5 mg/kg body weight, inclusive. Still more preferred therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgement of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different mAbs. Two or more monoclonal antibodies may provide an improved effect compared to a single antibody. Alternatively, a combination of an antibody with an antibody that binds a different antigen may provide an improved effect compared to a single antibody. Such mAb cocktails may have certain advantages inasmuch as they contain mAbs, which exploit different effector mechanisms or combine directly cytotoxic mAbs with mAbs that rely on immune effector functionality. Such mAbs in combination may exhibit synergistic therapeutic effects.

In another embodiment, the present invention provides an antibody which binds P2X7 wherein the antibody competes for binding to P2X7 with antibody BPM09 produced by the hybridoma AB253 deposited with the European Collection of Cell Cultures (ECACC) under Accession No. 06080101.

Antibodies which compete for binding with the anti-P2X7 antibody BPM09 to an antigen may be readily identified using routine competition binding assays known to those skilled in the art, such as the competitive ELISA immunoassay.

It is preferred that the level of competition is at least 50%, preferably at least 60% more preferably at least 70%. It is even more preferred that the level of competition is at least 80%, preferably at least 90% preferably at least 95%. It is most preferred that the level of competition is substantially 100%.

The term "% competition" refers to the decrease in binding which occurs in the presence of the competing antibody.

The following protocols are provided as non-limiting examples for the purpose of illustrating the invention.

EXAMPLE 1

Production of Monoclonal Antibodies

The preferred animal system for generating hybridomas is the murine system. Immunization protocols and techniques for isolation of immunized splenocytes for fusion are well known in the art. Fusion cell partners (e.g., murine myeloma cell lines SP2/0, NS0, NS1, rat myeloma Y3, rabbit myeloma 240E 1, human K6H6), fusion and screening procedures are also well known in the art (Galfre et al., 1977; Gefter et al., 1977; Galfre et al., 1979; dangl et al., 1982; Spieker-Polet et al., 1995).

(i) Hybridoma Generation

B cell-myeloma cell hybridomas were generated using splenocytes from immunised mice as follows:

Immunization: BALB/c mice (female, 8-10 weeks of age at first injection, CSIRO animal facility, North Ryde, Australia) were immunized with conjugate comprising human $P2X_7$ 200-216 linked to diphtheria toxoid (at a conjugation ratio of approximately 11:1) emulsified in adjuvant. The initial immunization was performed with conjugate in Montanide-QuilA-DEAE dextran, 4×50 µg/mL. Subsequent immunizations were performed at 2-4 weekly intervals with conjugate in ImmunEasy™ adjuvant (Qiagen), 2×50 µg/mL injections per mouse (1 intramuscularly and 1 subcutaneously), 200 µg/mL. After at least 3 immunization cycles, mice were injected with 20 µg conjugate intravenously in sterile phosphate-buffered saline.

Hybridoma generation: Four to five days after the intravenous boost, spleens were recovered and spleen cell suspensions prepared. Spleen cells were fused with SP2/0Ag14 myeloma cells by mixing at a ratio of 5:1 in a 50% solution of polyethylene glycol 1500 (Roche Cat No. 783 641) in serum-free medium (RPMI with 2 Mm L-glutamine, 1 mM sodium pyruvate, 50 IU/mL penicillin and 50 µg/mL streptomycin; Gibco). After incubation at 37° C. for 2 minutes, the cell suspension was diluted in serum-free medium, and pelleted by centrifugation (8 minutes, 70×g). Cells were cultivated in RPMI medium (as above, supplemented with 10% foetal bovine serum, HAT (Gibco) and 100 U/mL recombinant murine IL-6 (Peprotech). After 12-14 days, cell culture supernatants were assayed for reactivity by ELISA with solid-phase human $P2X_7$ 200-216 linked to bovine serum albumin (at a conjugation ratio of approximately 11:1). Positive wells were subcloned at limiting dilution.

From these positive wells the hybridoma producing antibody AB253 was isolated.

EXAMPLE 2

BPM09 is distinguished from other tumour-selective $P2X_7$ antibodies in that it results in superior immunohistochemical staining: strong staining of tumour tissue, with minimal staining of normal tissue.

Immunohistochemical Protocol/Results for AB253

Preparation of Tissue Sections

1. Sections (3 µm) from tumour blocks were floated onto 3-aminopropyltriethoxysilane (AES) coated heat resistant glass slides.
2. Slides were simultaneously dewaxed, endogenous peroxidase-blocked and heat induced epitope retrieval performed (Biocare Medical Universal Decloaker solution) and slides were stained in a Sequenza apparatus.

Staining of Tissue Sections with AB253

3. After rinsing with tris-buffered saline (Biocare Medical TBS automation wash buffer), sections were incubated with 80 pM AB253 for 60 minutes. After rinsing twice in TBS, Mach 4 Universal polymer (Biocare Medical) detection system was used, consisting of 15 minute incubation in anti-mouse IgG reagent, followed by rinsing once in TBS and incubation for 25 minutes in HRP-polymer and additional rinsing in TBS (×2).
4. After stringent washing and DAB (Dako) staining, BPM09-labeled slides were counter stained with haematoxylin (Mayer's with Lillie's modification, from Dako) for 1 minute, rinsed thoroughly and cover-slipped.
5. Photomicrographs were obtained using an Olympus BX41 with 10× objective (Olympus) and a Q Imaging Micropublisher 5 megapixel microscope camera.

FIG. 1 illustrates the binding of BPM09 to human prostate cancer tissue. In comparison, the amount of BPM09 antibody binding to normal tissue was minimal (data not shown), accounting for non-specific antibody binding only.

EXAMPLE 3

Anti-P2X$_7$ Competition ELISA

Materials

BSA-P2X$_7$ 200-216 PEPTIDE SEQUENCE (H-GHNYT-TRNILPGLNITC-NH$_2$ conjugated to Bovine Serum Albumin with Maleimidocaproyl-N-Hydroxysuccinimide (MCS) as the linker)

96 well ELISA plates

BSA (Albumin, Bovine Fraction V, Sigma Cat # A-9647)

Tween 20 (Polyoxyethylene-20-Sorbitan Monolaurate, Amresco Cat #0777-IL)

Biotinylated BPM09 (Biotinylation was performed on 1 mg of protein A-purified BPM09 with a 20-fold molar excess of NHS-LC-biotin Pierce Cat 3 21435 according to the manufacturer's instructions).

Secondary conjugate (Streptavidin conjugated to horseradish peroxidase (HRP), Zymed Cat# 434323)

Na$_2$CO$_3$, NaHCO$_3$, Na$_2$HPO$_4$, NaH$_2$PO$_4$, NaCl, citric acid monohydrate, tri-sodium citrate dihydrate, H$_2$O$_2$ ABTS (2,2'-Azino-bis(3-Ethylbenz-Thiazoline-6-Sulfonic acid) Diammonium Salt, Sigma Cat #A-1888)

ELISA plate reader

Solutions

Carbonate Coating Buffer pH 9.6

1.59 g of Na$_2$CO$_3$ and 2.93 g NAHCO$_3$ was made up to IL with distilled H$_2$O, after adjustment to pH 9.6.

0.1M PBS pH 7.2 (Stock Solution)

68.4 mL of a IM Na$_2$HPO$_4$ solution, 31.6 mL of a 1M NaH$_2$PO$_4$ solution and 88 g of NaCl was made up to 1 L with distilled H$_2$O after adjustment to pH 7.2.

0.01M PBS pH 7.2 (Working Concentration)

The 0.1M PBS solution was diluted (1/10) with distilled H$_2$O

Blocking Buffer

1% (w/v) BSA was added to 0.01M PBS pH 7.2

Antibody Diluent

1% (w/v) BSA and 0.05% (v/v) Tween 20 was added to 0.01M PBS pH 7.2

Wash Buffer 0.05% (v/v) Tween 20 was added to 0.01M PBS pH 7.2

Citrate Buffer (5×) (Stock Concentration)

21 g of citric acid monohydrate and 14.7 g tri-sodium citrate dehydrate was made up 150 mL with dH$_2$O after adjustment to pH to 4.4.

Substrate Solution 2.4 mL of Citrate buffer (5×), 240 µL ABTS solution [25 mg/mL in H$_2$O (50×)], 12 µL of H$_2$O$_2$, and made up to 12 mL with distilled H$_2$O.

Procedure

1. BSA-$_7$ was diluted to 3 µg/mL in Carbonate Coating Buffer, 100 µL added to each well of a 96 well plate, and incubated at 4° C. overnight in a humidified container.
2. The plate was washed in Wash Buffer (3×), then PBS (3×), and blotted onto a paper towel to remove leftover buffer.
3. The plate was blocked with 200 µL of Blocking buffer at room temperature, in a humidified container for a minimum of 1 hour.
4. Step 3 was repeated to wash the plate.
5. In a fresh 96 well plate, non-biotinylated BPM09, or an irrelevant specificity isotype-matched control was serially diluted in antibody diluent, and biotinylated BPM09 added (*0.63 µg/mL, final conc.).
   *biotinylated BPM09 concentration (0.6 µm/mL) was determined to give maximum binding in a preliminary ELISA conducted according to this protocol, with the omission of a competitor.
6. The antibody mixture (100 µL) was added to triplicate wells. Wells were included with no peptide coating to determine the background absorbance.
7. After 30 mins incubation at room temperature in a humidified container the plate was again washed according to step 3.
8. Streptavidin-HRP $1:2000) in antibody diluent (100 µL) was added to each well and incubated at room temperature in a humidified container with gentle mixing for 1 hour.
9. The plate was washed as in step 3 and the freshly prepared substrate solution (100 µL) was added to each well.
10. The colour reaction was allowed to develop for 15 min prior to measurement of the OD at 405 nm (ref. 620 nm) with an ELISA plate reader.

Figure 2:
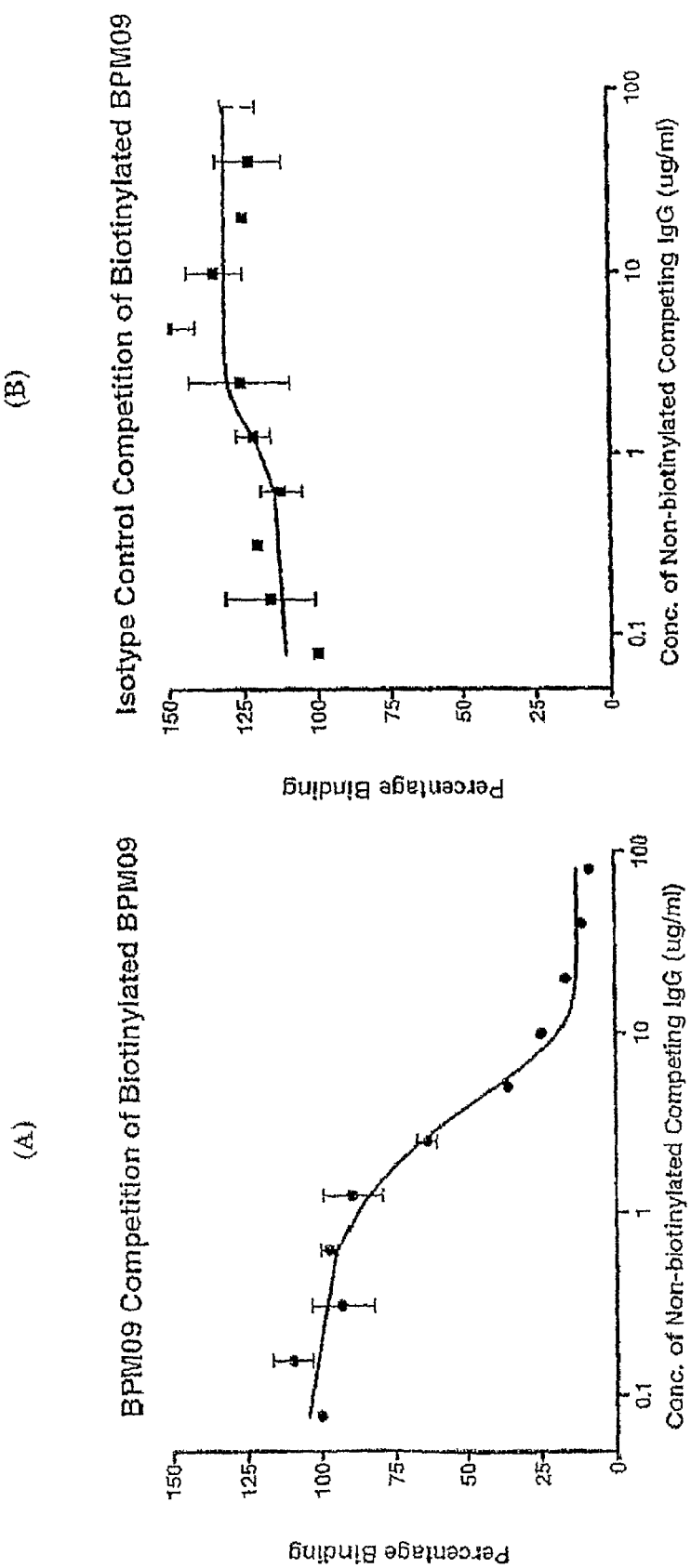
FIG. 2 shows (A) BPM09 competition of biotinylated BPM09, and (B) isotype control competition of biotinylated BPM09.

The results of the ELISA competition binding assays are indicated in FIG. 2. FIG. 2(A) shows that as the concentration of the non-biotinylated BPM09 antibody is increased, the overall binding of biotinylated BPM09 to the P2X$_7$ receptor sites decreases. Conversely, FIG. 2(B) shows the same competition binding assay performed using an immunoglobulin isotype-matched control where no effect on the binding of biotinylated antibodies is observed. These data clearly show the binding specificity of BPM09 antibody for P2X$_7$.

It will be understood that the invention disclosed and defined in this specification extends to all alternative embodiments of two or more of the individual features mentioned or evident from the text or drawings. All of these different combinations constitute various alternative aspects of the invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects and not restrictive.

The invention claimed is:

1. A hybridoma for producing an antibody that is capable of forming an immune complex with a non functional P2X7 receptor, the hybridoma being characterized in that it produces an antibody that has an affinity for a non functional P2X7 receptor expressed on a live cell of less than about $5\times10^6$ M$^{-1}$.

2. The hybridoma according to claim 1 wherein the affinity is about $5\times10^5$ M$^{-1}$ or less.

3. The hybridoma according to claim 1 wherein the affinity is about $5\times10^4$ M$^{-1}$ or less.

4. The hybridoma AB253 deposited with the European Collection of Cell Cultures (ECACC) under Accession no. 06080101.

5. An antibody produced by a hybridoma according to claim 1.

6. An antibody produced by the hybridoma according to claim 4.

7. The antibody according to claim 5 wherein the antibody binds to non functional P2X7 receptors but does not bind to functional P2X7 receptors.

8. An antigen binding fragment of an antibody according to claim 5.

9. An immune complex comprising the antibody of claim 5 or an antigen binding fragment thereof, bound to a non functional P2X7 receptor, monomer or fragment thereof.

10. The immune complex of claim 9 wherein the non functional P2X7 receptor, monomer or fragment thereof has an amino acid sequence shown in any one of SEQ ID NOs: 1 to 8.

11. A method for determining whether a cell, tissue or extra cellular body fluid includes a non functional P2X7 receptor, monomer or fragment thereof including:
   contacting a cell, tissue or extra cellular body fluid with the antibody of claim 5 or an antigen binding fragment thereof in conditions for forming an immune complex, and
   detecting whether an immune complex has been formed,
   wherein detection of an immune complex determines that a cell, tissue or extra-cellular body fluid includes a non functional P2X7 receptor, monomer or fragment thereof.

* * * * *